United States Patent [19]

Sachtler et al.

[11] Patent Number: 4,886,927
[45] Date of Patent: Dec. 12, 1989

[54] PROCESS FOR ISOMERIZATION OF ALKYLAROMATICS

[75] Inventors: J. W. Adriaan Sachtler, Des Plaines; R. Joe Lawson, Palatine; Susan L. Lambert, Rolling Meadows, all of Ill.

[73] Assignee: UOP, Des Plaines, Ill.

[21] Appl. No.: 281,424

[22] Filed: Dec. 8, 1988

Related U.S. Application Data

[62] Division of Ser. No. 109,019, Oct. 16, 1987, abandoned.

[51] Int. Cl.$^4$ ................................................. C07C 5/22
[52] U.S. Cl. ................................................... 585/48.1
[58] Field of Search ........................................ 585/481

[56] References Cited

U.S. PATENT DOCUMENTS

| | | | |
|---|---|---|---|
| 3,923,639 | 12/1975 | Ciric | 208/111 |
| 4,066,531 | 1/1978 | Owen et al. | 208/120 |
| 4,331,822 | 5/1982 | Onodera et al. | 585/482 |
| 4,485,185 | 11/1984 | Onodera et al. | 502/71 |
| 4,584,423 | 4/1986 | Nacamuli et al. | 585/481 |
| 4,599,475 | 7/1986 | Kresge et al. | 585/481 |

*Primary Examiner*—Curtis R. Davis
*Attorney, Agent, or Firm*—Thomas K. McBride; John F. Spears, Jr.

[57] ABSTRACT

This invention presents a process for isomerizing a non-equilibrium mixture of xylenes containing ethylbenzene, using a novel catalyst formulation comprising at least one Group VIII metal, a gallium-substituted pentasil zeolite and a matrix material of zirconia-alumina.

3 Claims, 1 Drawing Sheet

C$_8$ Ring Loss vs. Paraxylene Yield.

Paraxylene in Product / Total Xylenes (Mole %).

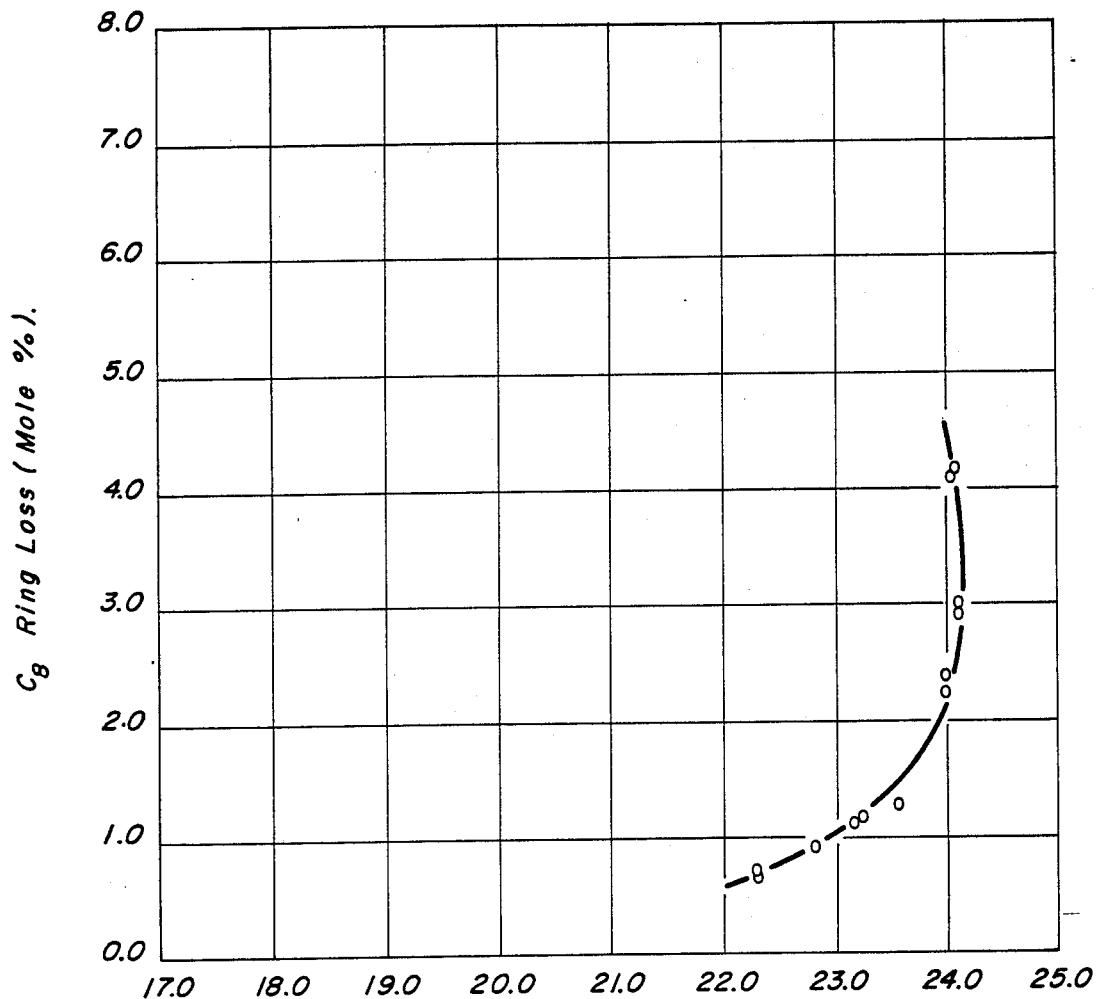

PROCESS FOR ISOMERIZATION OF ALKYLAROMATICS

CROSS-REFERENCE TO RELATED APPLICATION

This application is a division of prior copending application Ser. No. 109,019 filed Oct. 16, 1987 and now abandoned, the contents of which are incorporated herein by reference thereto.

FIELD OF THE INVENTION

This invention relates to an improved hydrocarbon-conversion process. More specifically, it relates to an improved process for the isomerization of xylenes and conversion of ethylbenzene.

BACKGROUND OF THE INVENTION

The xylenes, namely ortho-xylene, meta-xylene and para-xylene, are important chemicals and find wide and varied application in industry. Ortho-xylene is a reactant for the production of phthalic anhydride. Meta-xylene is used in the manufacture of plasticizers, azo dyes, wood preservers, etc. Para-xylene upon oxidation yields terephthalic acid which is used in the manufacture of synthetic textile fibers.

As a result of the important applications to which the individual xylene isomers are subjected, it is often very important to be able to produce high concentrations of a particular xylene. This can be accomplished by converting a non-equilibrium mixture of the xylene isomers, which mixture is low in the desired xylene isomer, to a mixture which approaches equilibrium concentrations. Various catalysts and processes have been devised to accomplish the isomerization process. For example, it is well known in the art that catalysts such as aluminum chloride, boron fluoride, liquid hydrofluoric acid, and mixtures of hydrofluoric acid and boron fluoride can be used to isomerize xylene mixtures.

Industrially, isomerization of xylenes and conversion of ethylbenzene is performed to produce paraxylene. A typical processing scheme for this objective comprises: (a) isomerizing a $C_8$ alkylaromatic mixture to near equilibrium in an isomerization reaction zone; (b) separating out para-xylene using, for example, molecular sieve technology to obtain a para-xylene rich stream and a stream rich in other xylenes; and, (c) recycling the stream rich in other xylenes to the isomerization reaction zone.

The present invention is particularly concerned with the isomerization reaction step which may be used in an overall process directed to para-xylene production. An important parameter to consider in this isomerization reaction step is the degree of approach to xylene equilibrium achieved. The approach to equilibrium that is used is an optimized compromise between high $C_8$ aromatic ring loss at high conversion (i.e. very close approach to equilibrium) and high utility costs due to the large recycle rate of unconverted ethylbenzene, ortho-xylene, and metaxylene. Also contributing to the recycle stream are $C_8$ naphthenes which result from the hydrogenation of the $C_8$ aromatics.

It is desirable to run the isomerization process as close to equilibrium as possible in order to maximize the para-xylene yield, however, associated with this is a greater cyclic $C_8$ loss due to side-reactions. Cyclic $C_8$ hydrocarbons include xylenes, ethylbenzene, and $C_8$ naphthenes. The correlation of cyclic $C_8$ loss versus the distance from xylene equilibrium is a measure of catalyst selectivity. Thus there is a strong incentive to develop a catalyst formulation which minimizes cyclic $C_8$ loss while maximizing para-xylene yield.

Numerous catalysts have been proposed for use in xylene isomerization processes such as mentioned above. More recently, a number of patents have disclosed the use of crystalline aluminosilicate zeolite-containing catalysts for isomerization and conversion of $C_8$ alkylaromatics. Crystalline aluminosilicates generally referred to as zeolites, may be represented by the empirical formula:

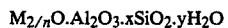
$$M_{2/n}O \cdot Al_2O_3 \cdot xSiO_2 \cdot yH_2O$$

in which n is the valence of M which is generally an element of Group I or II, in particular, sodium, potassium, magnesium, calcium, strontium, or barium, and x is generally equal to or greater than 2. Zeolites have skeletal structures which are made up of three-dimensional networks of $SiO_4$ and $AlO_4$ tetrahedra, corner-linked to each other by shared oxygen atoms. Zeolites with high $SiO_2/Al_2O_3$ ratios have received much attention as components for isomerization catalysts. Representative of zeolites having such high proportion of $SiO_2$ include mordenite and the ZSM varieties. It is also known in the art that zeolites of the ZSM series can be prepared with gallium atoms substituted for aluminum atoms, for example, see U.S. Pat. No. 4,585,641. In addition to the zeolite component, certain metal promoters and inorganic oxide matrices have been included in isomerization catalyst formulations. Examples of inorganic oxides include silica, alumina, and mixtures thereof. Metal promoters, such as Group VIII or Group III metals of the Periodic Table, have been used to provide a dehydrogenation functionality. The acidic function can be supplied by the inorganic oxide matrix, the zeolite, or both.

When employing catalysts containing zeolites for the isomerization of alkylaromatics, characteristics such as acid site strength, zeolite pore diameter, and zeolite surface area become important parameters to consider during formulation development. Variation of these characteristics in a way that reduces side-reactions, such as, transalkylation, is required in order to achieve acceptable levels of cyclic $C_8$ loss.

It has been found that, if a catalyst is formulated with the components, and in the manner set forth hereinafter, an improved process for the conversion of a non-equilibrium mixture of xylenes containing ethylbenzene is obtained.

OBJECTS AND EMBODIMENTS

A principal object of the present invention is to provide a novel process for the isomerization of isomerizable hydrocarbons. More specifically, the instant invention is aimed at a process for the isomerization of alkyl-aromatic hydrocarbons which results in minimal loss of the alkylaromatic hydrocarbons.

A broad embodiment of the invention is directed toward a process for the isomerization of isomerizable hydrocarbons utilizing a catalyst comprising at least one Group VIII metal component, a gallium-substituted pentasil zeolite, and a zirconia-alumina matrix.

Another embodiment is directed toward a process for the isomerization of a feed stream comprising a nonequilibrium mixture of xylenes containing ethylbenzene, which comprises contacting the feed in the presence of hydrogen at a temperature of from about 300° to 500° C., a pressure of from about 69 to about 6895 kPa (ga), a liquid hourly space velocity of from about 0.5 to about 10 hr$^{-1}$ with a catalyst comprising at least one Group VIII metal component, a gallium-substituted pentasil zeolite, and a zirconia-alumina matrix.

INFORMATION DISCLOSURE

The prior art recognizes numerous isomerization processes employing a variety of catalyst formulations. However, it is believed that none of the prior art processes recognizes the use of the catalyst formulation and method of making same which forms an integral part of the instant invention.

Related U.S. Pat. 4,331,822 and 4,485,185 (Onodera et al) teach the use of a catalyst containing silica-alumina pentasil zeolites having added thereto platinum and a second metal. However, neither reference recognizes gallium-substituted pentasil zeolites nor the use of a zirconia-alumina matrix. Another reference, U.S. Pat. 4,584,423 (Nacamuli et al), teaches a process for isomerizing a non-equilibrium mixture of xylenes containing ethylbenzene in the absence of hydrogen using a catalyst containing a pentasil zeolite wherein gallium may be substituted for aluminum. This reference makes no mention of the utility of either a zirconia-alumina matrix nor the incorporation of a Group VIII metal.

U.S. Pat. 4,482,773 (Chu et al) is directed to a process for isomerizing a mixture of xylenes and ethylbenzene with a ZSM-5 catalyst containing platinum and a Group IIA component. However, the reference does not recognize the utility of gallium substitution in the zeolite or of a zirconia-alumina matrix.

Isomerization of a xylenes/ethylbenzene mixture with a ZSM-5 catalyst also is disclosed in U.S. Pat. No. 4,584,423 (Nacamuli et al). This reference does disclose gallium as an alternative in the zeolite framework, but is not cognizant of a Group VIII metal or a zirconia-alumina matrix as catalyst constituents.

U.S. Pat. 4,255,288 (Cull et al) teaches a catalyst comprising a Y-type zeolite, alumina, zirconia, and at least one each of Group VIB and Group VIII metals. Hydrocracking and hydrodesulfurization tests show superior results for catalysts of the invention. The reference does not disclose a gallium substituted pentasil zeolite.

U.S. Pat. 3,923,639 (Ciric) is directed to a hydrocarbon cracking process utilizing a catalyst composition comprising a crystalline aluminosilicate ZSM-4 zeolite. Although the reference lists as possible components Group VIII metals and a variety of matrix materials, including alumina-zirconia, the reference is silent as to the utility of a gallium-substituted pentasil in combination with a Group VIII metal and zirconia-alumina matrix for the isomerization of alkylaromatic hydrocarbons.

The conversion of heavy reformate using a variety of different catalyst compositions, including silica-alumina containing pentasil zeolites, is taught in U.S. Pat. No. 4,066,531 (Owen et al). The utility of zirconia in combination with clay, alumina and silica is recognized as a suitable binding material. However, the reference is not cognizant of the utility of a gallium-substituted pentasil zeolite in combination with the other components of the instant invention.

In summary, it appears that the prior art only generally recognizes that zeolites have utility for isomerization of isomerizable alkylaromatics and that no single reference teaches nor suggests the invention claimed herein.

BRIEF DESCRIPTION OF THE DRAWING

The Figure graphically depicts isomerization performance expressed as a correlation between the cyclic $C_8$ hydrocarbons in mole percent lost due to side reactions and the para-xylene content in mole percent of the xylenes in the reaction product. Shown in this Figure are results for a catalyst made in accordance with the invention.

DETAILED DESCRIPTION OF THE INVENTION

As mentioned above, this invention is concerned with a process for the isomerization and conversion of a nonequilibrium mixture of $C_8$ aromatic hydrocarbons. This process utilizes a catalyst comprising at least one Group VIII metal component, a pentasil zeolite wherein a portion of aluminum atoms have been replaced with gallium atoms and a matrix material comprising zirconia-alumina. The instant invention provides a closer approach to xylene equilibrium, resulting in a greater yield of para-xylene without the high loss of $C_8$ aromatics common to prior art processes.

The process of this invention is applicable to the isomerization of isomerizable alkylaromatic hydrocarbons of the general formula:

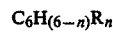

$$C_6H_{(6-n)}R_n$$

where n is an integer from 2 to 5 and R is $CH_3$, $C_2H_5$, $C_3H_7$, or $C_4H_9$, in any combination and including all the isomers thereof. Suitable alkylaromatic hydrocarbons include, for example, ortho-xylene, meta-xylene, para-xylene, ethylbenzene, ethyltoluenes, the trimethylbenzenes, the diethylbenzenes, the triethylbenzenes, methylpropylbenzenes, ethylpropylbenzenes, the diisopropyl-benzenes, the triisopropylbenzenes, etc., and mixtures thereof.

It is contemplated that any aromatic $C_8$ mixture containing ethylbenzene and xylene may be used as feed to the process of this invention. Generally, such mixture will have an ethylbenzene content in the approximate range of 5 to 50 wt. %, an ortho-xylene content in the approximate range of 0 to 35 wt. %, a meta-xylene content in the approximate range of 20 to 95 wt. % and a para-xylene content in the approximate range of 0 to 15 wt. %. It is preferred that the aforementioned $C_8$ aromatics comprise a non-equilibrium mixture. The feed to the instant process, in addition to $C_8$ aromatics, may contain nonaromatic hydrocarbons, i.e. naphthenes and paraffins in an amount up to 30 wt. %.

The alkylaromatic hydrocarbons for isomerization may be utilized as found in selective fractions from various refinery petroleum streams, e.g., as individual components or as certain boiling range fractions obtained by the selective fractionation and distillation of catalytically cracked gas oil. The process of this invention may be utilized for conversion of isomerizable aromatic hydrocarbons when they are present in minor quantities in various streams. The isomerizable aromatic hydrocarbons which may be used in the process of this invention need not be concentrated. The process of this invention allows the isomerization of alkylaromatic containing streams such as reformate to produce specified xylene isomers, particularly para-xylene, thus upgrading the reformate from its gasoline value to a high petrochemical value.

According to the process of the present invention, an alkylaromatic hydrocarbon charge stock, preferably in admixture with hydrogen, is contacted with a catalyst of the type hereinafter described in an alkylaromatic hydrocarbon isomerization zone. Contacting may be effected using the catalyst in a fixed bed system, a moving bed system, a fluidized bed system, or in a batch-type operation. In view of the danger of attrition loss of the valuable catalyst and of operational advantages, it is preferred to use a fixed bed system. In this system, a hydrogen-rich gas and the charge stock are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone. It is to be noted that the reactants may be contacted with the catalyst bed in either upward, downward, or radial flow fashion, and that the reactants may be in the liquid phase, a mixed liquid-vapor phase, or a vapor phase when contacted with the catalyst.

The process of this invention for isomerizing an isomerizable alkylaromatic hydrocarbon is preferably effected by contacting the alkylaromatic, in a reaction zone containing an isomerization catalyst as hereinafter described, with a fixed catalyst bed by passing the hydrocarbon in a down-flow or radial flow fashion through the bed, while maintaining the zone at proper alkylaromatic isomerization conditions such as a temperature in the range from about 0°–600° C. or more, and a pressure of about 101 kPa (abs) to about 10,340 kPa (ga) or more. Preferably, the operating temperature ranges from about 300°–500° C. and the pressure ranges from about 69 to about 6,895 kPa (ga). The hydrocarbon is passed, preferably, in admixture with hydrogen at a hydrogen/hydrocarbon mole ratio of about 0.5:1 to about 25:1 or more, and at a liquid hourly hydrocarbon space velocity of about 0.1 to about 20 $hr^{-1}$ or more, most preferably at 0.5 to 10 $hr^{-1}$. Other inert diluents such as nitrogen, argon, etc., may be present.

The particular product recovery scheme employed is not deemed to be critical to the instant invention. Any recovery scheme known in the art may be used. Typically, the reactor effluent will be condensed with the hydrogen and light hydrocarbon components removed therefrom by flash separation. The condensed liquid product is then subject to a fractionation procedure to further purify the desired liquid product. In some instances, it may be desirable to recover certain product species, such as ortho-xylene, by selective fractionation. In most instances, the liquid xylene product is processed to selectively recover the paraxylene isomer. Recovery of para-xylene can be performed by crystallization methods or most preferably by selective adsorption using crystalline aluminosilicates.

The catalyst of the instant invention contains at least one Group VIII metal component of the Periodic Table (see Cotton and Wilkinson, *Advanced Inoroanic Chemistry* (3rd Ed., 1972)). Preferably, this Group VIII metal is selected from the platinum group metals. Of the platinum group meals, which include palladium, rhodium, ruthenium, osmium and iridium, the use of platinum is preferred. The platinum group component may exist within the final catalyst composite as a compound such as an oxide, sulfide, halide, oxysulfide, etc., or as an elemental metal or in combination with one or more other ingredients of the catalyst. It is believed that the best results are obtained when substantially all the platinum group component exists in the elemental state. The platinum group component generally comprises from about 0.01 to about 2 wt. % of the final catalytic composite, calculated on an elemental basis. It is preferred that the platinum content of the catalyst be between about 0.1 and 1 wt. %. The preferred platinum group component is platinum, with palladium being the next preferred metal. The platinum group component may be incorporated into the catalyst composite in any suitable manner such as by coprecipitation or cogelation with the zirconia-alumina material, or by ion-exchange or impregnation of the zeolite, and by ion-exchange or impregnation of the zeolite and zirconia-alumina composite. The preferred method of preparing the catalyst normally involves the utilization of a water-soluble, decomposable compound of a platinum group metal to impregnate the zeolite and zirconia-alumina composite. For example, the platinum group component may be added to the composite by commingling the composite with an aqueous solution of chloroplatinic or chloropalladic acid. An acid such as hydrogen chloride is generally added to the impregnation solution to aid in the distribution of the platinum group component through the composite particles.

After addition of the Group VIII metal component to the zeolite and zirconia-alumina composite, the resultant composite is dried at a temperature ranging from about 100° to about 200° C. for a period of at least 2 to about 24 hours or more, and finally calcined or oxidized at a temperature ranging from about 450° to about 650° C. in air or oxygen atmosphere for a period of about 0.5 to about 10 hours in order to convert all of the metallic components to the corresponding oxide form. The resultant oxidative composite is preferably subjected to a substantially water-free reduction step prior to its use in the isomerization of hydrocarbons. This step is designed to selectively reduce the Group VIII metal component to the elemental metallic state and to ensure a uniform and finely divided dispersion of the metallic component throughout the catalyst. Preferably, a substantially pure and dry hydrogen stream (i.e. less than 20 vol. ppm $H_2O$) is used as the reducing agent in this step. The reducing agent is contacted with the oxidized catalyst at conditions including a reduction temperature ranging from about 200° to about 650° C. and a period of time of about 0.5 to 10 hours effective to reduce substantially all of the Group VIII metal component to the elemental metallic state.

The resulting reduced catalytic composite may, in some cases, be beneficially subjected to a presulfiding operation designed to incorporate in the catalytic composite from about 0.05 to about 0.5 wt. % sulfur calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 10° up to about 593° C. or more. It is generally a good practice to perform this presulfiding step operation under substantially water-free conditions.

The gallium-substituted pentasil zeolite utilized in the instant invention preferably has a formula (expressed in terms of mole ratios of oxides) as follows:

$$M_{2/n}O: W_2O_3: ySiO_2: zH_2O$$

wherein M is at least one cation of valence n, W is gallium and/or aluminum, y is at least 5, preferably at least 12, and z is from 0 to 40. The zeolite preferably has an X-ray diffraction characteristic of pentasil zeolites, which includes ZSM-5, ZSM-8, ZSM-11, ZSM-12, ZSM-23, and ZSM-35, with ZSM-5 being particularly preferred. "Pentasil" is a term used to describe a class of shape-selective zeolites. This novel class of zeolites is well known to the art and is typically characterized by a silica/alumina mole ratio of at least about 12. Suitable descriptions of the pentasils may be found in U.S. Pat. Nos. 4,159,282; 4,163,018; and 4,278,565, all of which are incorporated herein by reference. The zeolite framework may contain only gallium and silicon atoms or may contain a combination of gallium, aluminum, and silicon atoms. The gallium content, expressed as mole ratios of $SiO_2/Ga_2O_3$, may range from 20:1 to 400:1. The preferred gallium-substituted pentasil zeolite has a ZSM-5 structure with a gallium content ranging from 0.1 to 10 wt. % of the zeolite, most preferably ranging from 0.5 to 5 wt. %. The gallium-substituted pentasil zeolite may be prepared by crystallization from a reaction mixture comprising a silica source, a source of $Ga_2O_3$, a source of $Al_2O_3$ if desired, and optionally an organic template compound. It is believed that the preparation of zeolites is within the competence of one skilled in the art and a particular preparation method is not critical to the instant invention. It is preferred that the catalyst of the instant invention contain from 1 to 20 wt. % gallium-substituted ZSM-5 zeolite. Most preferably, the catalyst contains 5 to 15 wt. % of gallium-substituted ZSM-5 zeolite. In a preferred embodiment, the catalyst comprises 1 to 20 wt. % of gallium-substituted ZSM-5 zeolite and 80 to 99 wt. % zirconia-alumina matrix.

In accordance with the present invention, the catalyst contains a zirconia-alumina matrix. This matrix is a composite of two porous refractory inorganic oxides having basic chemical formulae of $ZrO_2$ and $Al_2O_3$, respectively. Suitable alumina materials are the crystalline aluminas materials are the crystalline aluminas known as gamma-, eta-, and theta-, with gamma- or eta-alumina being the most preferred. It is preferred that the matrix contains from about 90 to about 99 wt. % alumina. The zirconia portion of the matrix preferably constitutes from about 1 to about 10 wt. % of the matrix. Preferred physical properties of the matrix include an apparent bulk density of 0.3 to about 0.8 g/cc and surface area characteristics such that the average pore diameter is about 20 to 300 angstroms, the pore volume is about 0.1 to about 1 cc/g, and the surface area is about 100 to 500 m²/g.

Preparation of the matrix material may be performed in any suitable manner known to the art. A particularly preferred method of preparing the zirconia-alumina matrix is believed to result in a finished catalyst that exhibits superior performance when utilized for the conversion of hydrocarbons. This preferred method involves cogelation of zirconia and alumina in an intimate admixture with the gallium-substituted pentasil zeolite. The first step in the preparation method involves the formation of an alumina hydrosol. Any technique known to the art may be utilized to prepare the alumina hydrosol, however, a preferred method involves reacting aluminum metal with hydrochloric acid. The gallium-substituted pentasil zeolite is then added to the alumina hydrosol to form a homogeneous mixture. The amount of zeolite added is dependent on the ultimate end use of the finished catalyst. A preferred matrix/zeolite weight ratio in the finished catalyst ranges from 4:1 to 99:1, with a more preferred weight ratio range of 9:1 to 19:1. To the alumina sol and zeolite mixture is added a zirconia sol, for example, zirconium oxychloride, and to the resultant mixture is added a suitable gelling agent, such as, hexamethylenetetramine. It is believed that the order of combining the alumina sol, zirconia sol, zeolite, and gelling agent is unimportant. Therefore, any combination sequence of the ingredients should produce the catalyst of the instant invention. Once gelled, the composite may be formed into any desired shape such as spheres, pills, cakes, extrudates, powders, granules, tablets, etc. and utilized in any desired size. In a preferred embodiment, the resultant mixture is first shaped in the form of a sphere and then gelled.

For purposes of the present invention, a particularly preferred shape of the composite is a sphere, continuously manufactured by the well-known oil drop method. In summary, this method involves dropping the mixture of zeolite, alumina sol, zirconia sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50°–200° C. and subjected to a calcination procedure at a temperature of about 450°–700° C. for a period of about 1 to about 20 hours. This treatment effects conversion of the hydrogel to the corresponding zirconia-alumina matrix. In a preferred embodiment, the calcined composite is washed to remove any remaining alkali metal cations that may be present. The wash solution is preferably an aqueous ammonium solution, most preferably containing about 0.5% $NH_3$ in water. After washing at about 95° C., the composite is dried at about 110° C. See the teachings of U.S. Pat. No. 2,620,314 for additional details.

The following example is presented for purpose of illustration only and is not intended to limit the scope of the present invention.

EXAMPLE

This example presents test results obtained when the catalyst composition of the invention was evaluated in an isomerization process. The catalyst was evaluated using a pilot plant flow reactor processing a nonequilibrium $C_8$ aromatic feed comprising 52.0 wt. % meta-xylene, 18.5 wt. % ortho-xylene, 0.1 wt. % para-xylene, 21.3 wt. % ethylbenzene, and 0.1 wt. % toluene, with the balance being nonaromatic hydrocarbons. This feed was contacted with 100 cc of catalyst at a liquid hourly space velocity of 2, and a hydrogen/hydrocarbon mole ratio of 4. Reactor pressure and temperature were adjusted to cover a range of conversion values in order to develop the relationship between $C_8$ ring loss and approach to xylene equilibrium (as determined by product para-xylene to total xylene weight ratio). At the same time, at each temperature, the pressure was chosen to maintain a constant mole ratio of $C_8$ naphthenes to $C_8$ aromatics of approximately 0.06.

A quantity of gallium-substituted pentasil zeolite having an X-ray diffraction pattern equivalent to that of ZSM-5 was prepared by adding a silica source, Ludox HS-40, to an aqueous solution containing an organic template, tetrapropylammonium bromide. The weight ratio of silica to template was about 1:1. A solution of sodium gallate was added to the silica and template mixture in an amount to give about 1.0 wt. % gallium based on the finished zeolite. The resultant mixture was autoclaved at about 150° C. for approximately 140 hours. The zeolite obtained was washed, filtered and dried to yield a gallium-substituted pentasil zeolite containing approximately 1.3 wt. % Ga.

A portion of the zeolite described above was mixed with alumina hydrosol, prepared by digesting metallic aluminum in hydrochloric acid, to yield a zeolite content in the finished catalyst equal to about 10 wt. %. To this mixture was added enough zirconium oxychloride sol, containing approximately 20 wt. % $ZrO_2$, such that the finished zeolite zirconia-alumina composite contained approximately 5 wt. % $ZrO_2$. Finally, a solution of hexamethylenetetramine was added as a gelling agent. The final mixture was dispersed as droplets into an oil bath at a temperature of about 95° C. The droplets remained in the oil bath until they formed hydrogel spheres. The spheres were removed from the oil bath and washed with an aqueous solution containing about 0.5 wt. % ammonia. The spheres were then air dried at 110° C. for about 12 hours and then calcined in air at a temperature of about 650° C. After calcination, the composite was washed with 0.5% $NH_3/H_2O$ solution at 95° C. and then oven-dried at 110° C.

The dried spheres were next impregnated with a solution of chloroplatinic acid, containing 2 wt. % hydrochloric acid (based on the calcined spheres), to yield a final platinum concentration of 0.28 wt. %. The impregnated spheres were oxidized and chloride adjusted at 525° C., reduced in molecular hydrogen at 565° C., and then sulfided with hydrogen sulfide at ambient temperature to a target sulfur level of 0.1 wt. %.

The Figure graphically presents the isomerization process performance using the catalyst of the invention. In the Figure, the X-axis is the concentration of para-xylene in the product, expressed as mole percent relative to the total xylenes in the product. The Y-axis represents the amount of $C_8$ cyclic hydrocarbons lost due to side reactions. This parameter is defined as the sum of $C_8$ aromatics and naphthenes in the feed minus the amount of $C_8$ aromatics and naphthenes in the product divided by the $C_8$ aromatics and naphthenes in the feed.

What is claimed is:

1. A process for the isomerization of a non-equilibrium feed mixture of xylenes containing ethylbenzene comprising contacting the feed mixture in the presence of hydrogen at isomerization process conditions with a catalyst comprising at least one Group VIII metal component, a gallium-substituted zeolite having an x-ray diffraction pattern equivalent to ZSM-5, and a zirconia-alumina matrix.

2. The process of claim 1 wherein the isomerization process conditions comprise a temperature of from about 300° to about 500° C., a pressure of from about 69 to about 6895 kPa (ga), a liquid hourly space velocity of from about 0.5 to 10 $hr^{-1}$ and a hydrogen to hydrocarbon mole ratio of about 0.5:1 to about 25:1.

3. The process of claim 1 further characterized in that the Group VIII metal component comprises from about 0.1 to 5 wt. % platinum.

* * * * *